United States Patent [19]

Hasegawa et al.

[11] Patent Number: 5,063,255
[45] Date of Patent: Nov. 5, 1991

[54] PHOTOPOLYMERIZABLE TYPE RESIN COMPOSITIONS FOR DENTAL PURPOSES

[75] Inventors: Akira Hasegawa, Inuyama; Hiroshi Mori, Chita; Tatsuhiko Takahashi; Yasuyuki Sano, both of Nagoya, all of Japan

[73] Assignee: G-C Toshi Kogyo Corporation, Aichi, Japan

[21] Appl. No.: 430,590

[22] Filed: Nov. 1, 1989

[30] Foreign Application Priority Data

Nov. 18, 1988 [JP] Japan .................. 63-290160

[51] Int. Cl.$^5$ .................. C08F 18/02; C08F 118/02; C08F 218/02
[52] U.S. Cl. .................. 522/96; 522/908; 523/109; 526/320
[58] Field of Search .................. 522/96, 908, 90; 523/109; 526/320

[56] References Cited

U.S. PATENT DOCUMENTS

| | | | |
|---|---|---|---|
| 4,110,184 | 8/1978 | Dart et al. | 522/96 |
| 4,235,686 | 11/1980 | Dart et al. | 430/284 |
| 4,347,174 | 8/1982 | Nagase et al. | 522/96 |
| 4,457,818 | 7/1984 | Denyer et al. | 522/96 |
| 4,459,193 | 7/1984 | Ratcliffe et al. | 522/96 |
| 4,491,453 | 1/1985 | Koblitz et al. | 522/96 |
| 4,598,009 | 7/1986 | Christie et al. | 428/172 |
| 4,771,084 | 9/1988 | Kubota et al. | 522/96 |
| 4,795,823 | 1/1989 | Schmidt et al. | 522/908 |

Primary Examiner—Marion E. McCamish
Assistant Examiner—Susan Berman
Attorney, Agent, or Firm—Oblon, Spivak, McClelland, Maier & Neustadt

[57] ABSTRACT

A dental photopolymerizable type resin composition is provided, which comprises (a) a photopolymerizable compound that has therein at least one ethylenically unsaturated double bond and is a solid either crystalline or amorphous at 40° C. or lower, (b) an inorganic filler, (c) a photopolymerization initiator, and (d) a reducing agent. That compound may be a mono- or poly-functional (meth)acrylate.

9 Claims, 1 Drawing Sheet

PHOTOPOLYMERIZABLE TYPE RESIN COMPOSITIONS FOR DENTAL PURPOSES

BACKGROUND OF THE INVENTION

1. Field of the Invention

The present invention relates to a photopolymerizable type of dental resin composition which, when preparing full dentures or partial dentures for dentes defects, is provided to make base plates for bite plates used for the purpose of determining the relative positions of the upper and lower jaws, individual trays that are impression trays for individual patients to take final impressions and orthodontic resins to ameliorate malocclusion, restore cleft palate and cheiloschisis and ameliorate bottle mouths.

2. Prior Art

For the preparation of base plates for bite plates and individual trays, that are an impression tray for each individual patient, used so as to make full dentures or partial dentures for dentes defects as well as orthodontic resins, there has heretofore been used a powder/liquid type of cold-polymerizable resin in which polymethyl methacrylate and methyl methacrylate are mainly contained as the powder and liquid ingredients, respectively. The powder ingredient containing benzoyl peroxide as an initiator is mixed with the liquid ingredient containing a tertiary amine such as N,N'-dimethyl-p-toluidine as an accelerator, thereby initiating the reaction involved. Referring to the use of such resins, the required amounts of powder and liquid are weighed out and sufficiently mixed together in a mixing rubber cup with the use of a spatula. A resin paste, remaining admixed but not cured, is spread into a sheet form having a suitable thickness of, e.g., 1.5 to 2.5 mm for base plates or orthodontic resins and 1.0 to 5.0 mm for individual trays, and is then fitted under pressure onto a master cast of gypsum, to wait its curing. The orthodontic resin is used in combination with an orthodontic appliance—defined in a narrow sense—for the purpose of tooth movement, an orthopaedic appliance for the purpose of skeletal modification and a retaining appliance for the purpose of retention after minor tooth movement. In addition to the use of the resin in sheet forms, as mentioned above, the liquid may be applied direct onto the master cast of gypsum, followed by dusting of the powder. In this case, transparency is an important factor for the orthodontic resin and a pressure pot (about 2.5 to 3.0 kg/cm²) must be used to avoid the occurrence of air bubbles. Other materials such as thermoplastic resins or waxes may be used for base plates or individual trays. In recent years, materials for photopolymerizable base plates and individual trays in sheet forms have been developed. However, such materials are still far from perfection in terms of compatibility accuracy and maneuverability, since they use as the main ingredient monomer a liquid viscous at 40° C. or lower.

Cold-polymerizable type resins such as resins for the above powder/liquid type of base plates or individual trays or orthodontic resins, materials for photopolymerizable base plates or individual trays in sheet forms in which a liquid viscous at 40° C. or lower is used as the main ingredient monomer or materials for base plates or individual trays formed of thermoplastic resins or waxes have involved such problems as described below.

1. With the powder/liquid type of resin, it is required to weigh out the required amounts of powder and liquid, to admixing them together in a mixing rubber cup with the use of a spatula and to have the resulting resin paste in a sheet form. It is then impossible to keep the thickness of the sheet constant, because the sheet made pasty is a material so plastic that as soon as it is picked up by hand or fingers, it deforms and is thus partly thinned. Hence, it is likely that the base plates or individual trays or the orthodontic resin may break off due to stress concentrating upon the thinned portions.

2. The powder/liquid type of cold-polymerizable resin undergoes an exothermic curing reaction. Although a maximum temperature of exothermic heat varies depending upon the proportion of the powder and liquid to be admixed together, it reaches as high as about 60° C. when 2 g of the powder are used per 1 ml of the liquid. Such heat generation results in thermal deformation which is so much increased that it produces an adverse influence upon the fitting of the base plate or orthodontic resin with respect to a master cast of gypsum.

3. The powder/liquid type of cold-polymerizable resin or the photopolymerizable sheet using as the main ingredient a viscous liquid at normal temperature shrinks considerably upon polymerization. The powder/liquid type of resin shows a linear shrinkage of 2 to 3% due to its combined heat shrinkage/shrinkage-upon-polymerization, whereas the photopolymerizable sheet using as the main ingredient a viscous liquid at 40° C. or lower exhibits a linear shrinkage of 0.8 to 1.5% by shrinkage-upon-polymerization alone in the absence of substantial heat generation. This means that the compatibility of the base plate or orthodontic resin with respect to a master cast of gypsum is adversely affected.

4. The photopolymerizable sheet using as the main ingredient monomer a liquid viscous at 40° C. or lower is very poor in maneuverability, since it becomes sticky on its surface when fitted under pressure onto a master cast of gypsum direct by hand or fingers. Moreover, the liquid viscous at 40° C. or lower is liable to adhere to hands and fingers, possibly inducing eczema or an eruption on the skin.

5. When making an orthodontic resin with the powder/liquid type of cold-polymerizable resin, it has to be necessarily polymerized under pressure in a pressure pot so as to attain transparency by the removal of air bubbles. Since it is thus difficult to determine the time when the powder/liquid is to be made pasty and when the resin paste is to be pressurized in the pressure pot, some length of time and skill are required to obtain the orthodontic resin. Other materials for base plates or indiviudal trays formed of thermoplastic resins or waxes are also repeatedly softened by heat and fitted under pressure onto a master cast of gypsum to improve their compatibility. Hence, considerably longer length of time and skill are similarly required to for the accommodation in sophisticated cases such as in the case of partial dentures.

6. Materials for base plates or individual trays formed of thermoplastic resins or waxes have some strength in a thermally softened state, but have the property of deforming plastically or becoming very fragile when restored to normal temperature at which they are actually used. For the base plates, this implies that their strength is limited with respect to an occlusal pressure exerted during bite taking, so that they may break off or deform, thus making it impossible to prepare dentures of good compatibility. For the individual trays, this means that they may break off or deform, or make it impossible to achieve accurate impression taking. With the thermoplastic resins, neither is it possible to achieve myoplasty for which a compound softened at 70° to 80° C. is used and, hence, it is not possible to obtain any functional and precise master cast of gypsum. Thus, subsequent dental operations cannot be continued.

SUMMARY OF THE INVENTION

As a result of intensive and extensive studies made to solve the above problems, the present inventors have now found that they are all solved by developing resins for photopolymerizable base plates, individual trays and orthodontics making use of a photopolymerizable compound which has therein at least one ethylenically unsaturated double bond and is a solid at 40° C. and lower, either crystalline or amorphous.

Reference will now be made to some specific ways to solve the above problems.

1. The resin for photopolymerizable base plates, individual trays and orthodontics, which contains as the main ingredient a photopolymerizable compound having at least one ethylenically unsaturated double bond and being a crystalline or amorphous solid at 40° C. and lower, is previously molded into a sheet (having a thickness of 1.5 to 2.5 mm for base plates or orthodontics resins or 1.0 to 5.0 mm for individual trays). Because it contains as the main component a monomer which is a crystalline or amorphous solid at 40° C. and lower, it is unlikely to be softened and thinly spread at bodily temperature (37° C.) by touch with the hand or fingers. Moreover, since the resin is previously kept constant in thickness, its thickness remains more uniform, as compared with the case where the powder/liquid type of resin is formed into a sheet. Thus, there is no possibility of breaking-off due to stress concentrating on thin portions.

2. The resin for photopolymerizable base plates, individual trays and orthodontics, which contains as the main ingredient a photopolymerizable compound having at least one ethylenically unsaturated double bond and being a crystalline or amorphous solid at 40° C. and lower generates less heat than does the powder/liquid type of cold-polymerizable resin composed mainly of polymethyl methacrylate and methyl methacrylate. Consequently, when 3 g of a sample according to the present invention are cured with Labolight LV-1 manufactured by GC Dental Industries, the temperature of exothermic heat only rises to about 30° C. Since no substantial thermal deformation occurs due to the generation of heat, therefore, no problem arises at all in connection with the compatibility of a master cast of gypsum with respect to the base plates or orthodontic resins.

3. In general, phase transitions from gas to liquid, liquid to solid and gas to solid, there is a large change, i.e. shrinkage, in volume. For the reason that the photopolymerizable compound according to the present invention is a crystalline or amorphous solid at 40° C. and lower, however, the resin for base plates or orthodontics according to the present invention undergoes a phase transition from solid to solid. Thus, there is no substantial change in volume, i.e. shrinkage, upon polymerization. Nor does any problem arise at all in connection with the compatibility of a master cast of gypsum with respect to the resin for base plates or orthodontics.

4. Since the resin for base plates, individual trays and orthodontics according to the present invention uses as its main component a photopolymerizable compound that is a crystalline or amorphous solid at 40° C. and lower and has therein at least one ethylenically unsaturated double bond, it shows little surface stickiness when comparing with a photopolymerizable sheet using a liquid viscous at 40° C. or lower and thus is greatly improved in terms of maneuverability when a sheet formed thereof is fitted under pressure onto a master cast of gypsum. Since that resin hardly adheres to the skin, neither eczema nor eruption is induced on the skin.

5. The photopolymerizable resin for orthodontics containing as its major ingredient a photopolymerizable compound that has therein at least one ethylenically unsaturated double bond and is a solid either crystalline or amorphous at 40° C. and lower is of a paste type and is previously defoamed such that there is no need of any pressurization in a pressure pot for the purpose of the removal of air bubbles. Further, since no care is taken of the time when the resin is to be made pasty, it is possible to make an orthodontic resin of good compatibility within a short span of time but without recourse to any skilled hands. Still further, owing to such repeated softening-by-heat which can be dispensed with as required for thermoplastic resins or waxes, it is easily achievable to prepare base plates or individual trays even for sophisticated cases such as the case of partial dentures.

6. The material for photopolymerizable base plates and individual trays according to the present invention, which contains as its primary component a photopolymerizable compound that has therein at least one ethylenically unsaturated double bond and is a solid either crystalline or amorphous at 40° C. and lower, is composite with an inorganic filler treated on its surface, and is thus superior in its mechanical properties to thermoplastic resins or waxes. When used for base plates, on the one hand, it can thus sufficiently stand up to an occlusal pressure during bite taking. When used for individual trays, on the other hand, it is possible to take precise impressions owing to absence of fear of breaking-off or deformation.

Of the photopolymerizable compounds which have therein at least one ethylenically unsaturated double bond and are a solid either crystalline or amorphous at 40° C. and lower, the monofunctional methacrylates and acrylates typically includes methoxypolyethylene glycol 1000 methacrylate and methoxypolyethylene glycol 1000 acrylate, respectively. Examples of the polyfunctional methacrylates involve a reaction product of di-isocyanate methylbenzene with 2-hydroxyethyl methacrylate, a reaction product of di-isocyanate methylcyclohexane with 2-hydroxyethyl methacrylate, a reaction product of isophorone di-isocyanate with 2-hydroxyethyl methacrylate, a reaction product of hexamethylene di-isocyanate with 2-hydroxyethyl methacrylate, a reaction product of hexamethylene di-isocyanate with 2-hydroxypropyl methacrylate, a reaction product of hexamethylene di-isocyanate with 3-chloro-2-hydroxypropyl methacrylate, a reaction product of methylene-bis(4-cyclohexyl isocyanate) with 2-hydroxyethyl methacrylate, tris(methacryloxyethyl isocyanate) and polyethylene glycol 1000 dimethacrylate. Example of the polyfunctional acrylates include tris(acryloxyethyl isocyanate), pentaerythritol tetracrylate and pentaerythritol triacrylate. Suitable are also the polyfunctional acrylates and methacrylates having the following structural formulae:

wherein $R_1$, $R_2$ and $R_3$ each stand for an alkyl group, and wherein R is an alkyl group.

The inorganic fillers used in the present invention may include powdery quartz, powdery alumina, powdery glass, kaolin, talc, calcium carbonate, barium aluminosilicate glass, titanium oxide, borosilicate glass, colloidal silica powders, a so-called organic composite filler obtained by the compaction and pulverization of colloidal silica with polymers, alumina whiskers, beryllium oxide whiskers, boron carbide whiskers, silicon carbide whiskers, silicon nitride whiskers, various metal (chromium, copper, iron and nickel) whiskers and so on.

Such inorganic fillers may selectively be used in amounts of 5 to 500 parts by weight, preferably 50 to 200 parts by weight per 100 parts by weight of the photopolymerizable compound that has therein at least one ethylenically unsaturated double bond and is a solid either crystalline or amorphous at 40° C. and lower.

Prior to the mixing of the above inorganic filler with a binder resin, it is preferable that such filler is treated with a coupling agent capable of reacting with both the filler and binder resin. The coupling agents used may include those based on organofunctional silane, titanate and aluminate. Alternatively, the inorganic filler may be grafted on its surface for bonding to the binder resin.

The organofunctional silane coupling agents used may include γ-methacryloxypropyl trimethoxy silane, vinyl trichlorosilane, vinyl-tris(β-methoxyethoxy)silane, γ-methacryloxypropylmethyl dimethoxy silane, γ-glycydoxypropyl trimethoxy silane, γ-chloropropyl trimethoxy silane, β-(3,4-epoxycyclohexyl)ethyl trimethoxy silane, trimethyl chlorosilane, dimethyl dichlorosilane, hexamethyl disilane, γ-aminopropyl triethoxyl silane, N-β-(aminoethoxy)-γ-aminopropyl trimethoxy silane, γ-ureidopropyl trimethoxy silane and so on.

The inorganic filler may be treated on its surface with such coupling agents in any specific but not exclusive methods. Although varying with the properties required and not exclusively specified, the amount of such coupling agents to be used is suitably in a range of generally 0.1 to 20 parts by weight, preferably 1 to 10 parts by weight per 100 parts of the inorganic filler.

The photopolymerization initiators effectively used may include α-diketone compounds, ketal compounds, anthraquinone compounds, thioxanthon compounds and benzoin alkyl ether compounds. Specifically, the α-diketone compounds are effectively d,l-camphorquinone, benzil, diacetyl, acenaphthenequinone, 9,10-phenanthrenequinone and the like. Among others, particular preference is given to d,l-camphorquinone and benzil. The ketal compounds are effectively benzyl dimethyl ketal, benzil diethyl ketal, benzil dipropyl ketal, benzil-di(β-phenylethyl)ketal, benzil-di(2-methoxyethyl)ketal, benzil-di(2-ethoxyethyl)ketal, benzil-di(2-methoxyethoxyethyl)ketal, benzil-di(2-ethoxyethoxyethyl)ketal, 4,4'-dimethylbenzil diethyl ketal, 2,2'-dimethoxy benzil diethyl ketal, 4,4'-dichlorobenzil diethyl ketal, 4,4'-dichlorobenzil dipropyl ketal and so on. Among others, particular preference is given to benzyl dimethyl ketal, benzil diethyl ketal, benzil di(2-methoxyethyl)ketal and 4,4'-dimethylbenzil dimethyl ketal.

The anthraquinone compounds to be effectively used are anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone and the like. Among others, particular preference is given to anthraquinone, 1-chloroanthraquinone and 1,2-benzanthraquinone. The thioxanthon compounds to be effectively used are thioxanthon, 2-chlorothioxanthon, 2-isopropylthioxanthon, 2-nitrothioxanthon, 2-methylthioxanthon, 2,4-dimethylthioxanthon, 2,4-diethylthioxanthon, 2,4-diisopropylthioxanthon, 2-chloro-7-trifluoromethylthioxanthon, thioxanthon-10,10-dioxide, thioxanthon-10-oxide and so on. Among others, particular preference is given to thioxanthon, 2-chlorothioxanthon, 2,4-dimethylthioxanthon, 2,4-diethylthioxanthon and 2,4-di-isopropylthioxanthon.

The benzoin alkyl ether compounds to be effectively used are benzoin methyl ether, benzoin ethyl ether, benzoin isopropyl ether, benzoin-n-butyl ether, benzoin butyl ether and the like. Among others, particular preference is given to benzoin butyl ether.

The above photopolymerization initiators may be used alone or in combination of two or more. Preferably, such photopolymerization initiators may be incorporated in an amount of 0.001 to 5 parts by weight per 100 parts by weight of the photopolymerizable compound that has therein at least one ethylenically unsaturated double bond and is a solid either crystalline or amorphous at 40° C. and lower. At below 0.001 part by weight, such initiators are so poor in reactivity that the length of curing time is increased with a decrease in curing depth whereas, at higher than 5 parts by weight, an excessive part of the catalyst acts as a plasticizer to decrease the strength of cured products.

The reducing agent used in the present invention is of such a reducing capability that, although it reduces a photosensitizer when the latter is kept excited, it cannot take part in the reduction of the photosensitizer when the latter is not excited by active energy beams. The reducing agents may be primary, secondary or tertiary amines, as expressed in terms of:

wherein two or one or none of R, R' and R" groups may be a hydrogen atom or hydrogen atoms. One or more groups R, R' and R" may be identical or different hydrocarbon groups. The hydrocarbon groups may be each an alkyl, cycloalkyl, hydroxyalkyl or aralkyl group. Preferably, the groups R, R' and R" may be each an alkyl group having 1 to 10 carbon atoms.

Suitable examples of the reducing agents wherein one or more units R, R' and R" are a hydrocarbon group may include propylamine, n-butylamine, pentylamine, hexylamine, dimethylamine, diethylamine, dipropylamine, di-n-butylamine, dipentylamine, 2-dimethylaminoethanol, trimethylamine, triethylamine, tripropylamine, tri-n-butylamine, tripentylamine, dimethylaminoethyl methacrylate, diethylaminoethyl methacrylate, triethanolamine and long-chain aliphatic amines.

Examples of the reducing agents containing the aromatic group include N,N'-dimethylaniline, N,N'-dimethyl-p-toluidine, p-tolyldiethanolamine, m-tolyldiethanolamine, N-methyldiphenylamine, 2-dimethylaminobenzoic acid ethyl ester, 4-dimethylaminobenzoic acid ethyl ester, 4-dimethylaminobenzoic acid methyl ester, 4-dimethylaminobenzoic acid butyl ester, 4-dimethylaminobenzoic acid 2-ethylhexyl ester, 4-dimethylaminobenzoic acid isoamyl ester and so on.

Use may also be made of such diamines as expressed in terms of:

wherein n is an integer of 2 or more and R, R', R" and R'", different or identical, may be a hydrogen atom or a hydrocarbon group, especially, an alkyl group. Typical of such type of reducing agents are ethylenediamine, trimethylenediamine, tetramethylenediamine, pentamethylenediamine or hexamethylenediamine or their N-hydrocarbon group substituted derivatives, especially, N-alkyl derivatives.

Examples of the reducing agents wherein an element N forms a part of a cyclic system may include piperidine and its N-hydrocarbon derivative. Other reducing agents may include triarylamine, allylthiourea, aromatic sulfites, 5-alkyl-or 5-aryl barbituric acid.

Of these reducing agents, preference is given to dimethylaminoethyl methacrylate, triethanolamine, 4-dimethylaminobenzoic acid methyl ester and 4-dimethylaminobenzoic acid ethyl ester.

Preferably, the amount of such reducing agents to be added is in a range of 0.01 to 10 parts by weight per 100 parts by weight of the photopolymerizable compound that has therein at least one ethylenically unsaturated double bond and is a solid either crystalline or amorphous at 40° C. and lower. At below 0.01 part by weight, on the one hand, such reducing agents are so poor in reactivity that the length of curing time is increased with a decrease in curing depth. At higher than 10 parts by weight, on the other hand, they are so poor in storage stability that the length of time allowed for dental manipulations under ordinary indoor illumination is considerably decreased.

BRIEF DESCRIPTION OF THE DRAWINGS

A single drawing is a schematic illustration of the sample and master cast of gypsum used in Experiment 7 with each unit in mm.

EXAMPLES

In the examples and comparison examples, a number of samples were prepared to perform Experiments 1 to 7, thereby confirming the effects of the present invention. It is to be noted, however, that the present invention is by no means limited to the examples. In a table to be given later, the results of the examples and comparative examples are summarized. Various physical properties were evaluated by the following experiments.

Experiment 1—Maneuverability Before Curing

Free from stickiness but rich in flexibility.

Experiment 2—Bending Strength After Curing [I.S.O. 4049 (25×2×2 mm)]

Some samples using the ketal and benzoin alkyl ether compounds were irradiated with GC Permacure UC-I—trade name—manufactured by GC Dental Industries for 20 minutes. Others were all irradiated with GC Labolight LV-1—trade name—manufactured by GC Dental Industries for 5 minutes. A C.H.S. of 1 mm/min was applied.

Experiment 3—Curing Depth

Some samples using the ketal and benzoin alkyl ether compounds were irradiated with GC Permacure UC-I—trade name—manufactured by GC Dental Industries for 20 minutes, and uncured matter was wiped out with a gauze after washing with ethyl alcohol. Others were all irradiated with GC Light VL-1—trade name—manufactured by GC Dental Industries for 40 seconds, and uncured matter was wiped out with a gauze after washing with ethyl alcohol.

Experiment 4—Shrinkage Upon Polymerization

Some samples using the ketal and benzoin alkyl ether compounds were irradiated with GC Permacure UC-I—trade name—manufactured by GC Dental Industries for 20 minutes. Others were all irradiated with GC Labolight LV-1—trade name—manufactured by GC Dental Industries for 5 minutes. The shrinkage upon polymerization is then evaluated in terms of a linear shrikage (%) according to the following equation:

$$\text{Linear Shrinkage (\%)} = \frac{l_0 - l}{l_0} \times 100$$

wherein $l_0$: distance (mm) between the initial reference points prior to irradiation, and
l: distance (mm) between the reference points after irradiation.

Reading was then carried out with an accuracy of 1 μm.

Two aluminium foils, each cut into a triangle, were gently placed and pressed down upon each sample of 25×2×2 mm in size with fingers. $l_0$ and l readings were precisely found under a projector or a reading microscope.

Experiment 5—Necessity of Pressure Pot

Investigation was made on whether or not a pressure pot was needed to prevent the occurrence of air bubbles when preparing an orthodontic resin. As the pressure pot, GC Permapot—trade name—manufactured by GC Dental Industries was used at a pressure of 2.5 kg/cm².

Experiment 6—Maximum Temperature of Exothermic Heat During Curing

Some paste type of ketal and benzoin alkyl ether-containing samples, each weighing 3 g, were irradiated with GC Permacure UC-I—trade name—manufactured by GC Dental Industries. Others were all irradiated with GC Light VL-I—trade name—manufactured by GC Dental Industries. The temperature of exothermic heat was measured during curing with a thermistor thermometer inserted into the center of each sample. Such irradiation was continued until a maximum temperature of exothermic heat was read.

Experiment 7

Figure 1:
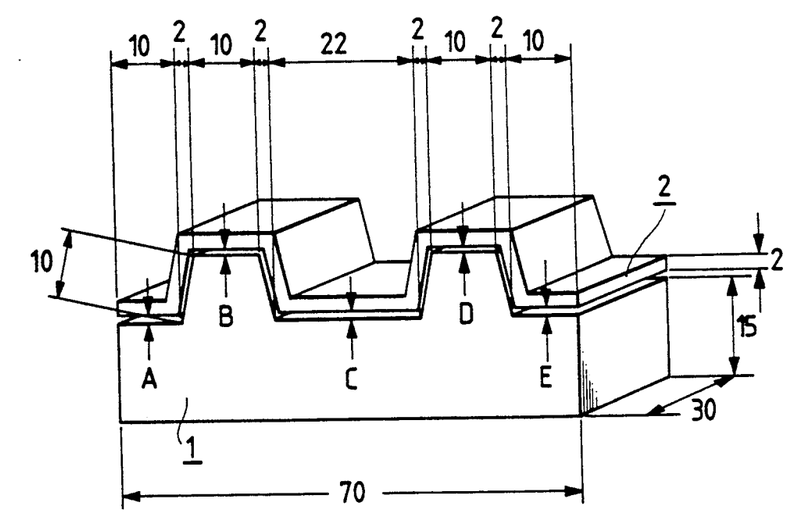

By hand or fingers, each sheet-form sample 2 of 2 mm in thickness was fitted under pressure onto a master cast 1 formed of anhydrite (available from GC Dental Industries under the trade name of GC New Plastone) in such a careful manner that no gap remained. Some samples 2 containing the ketal and benzoin alkyl ether compounds were irradiated with GC Permacure UC-I—trade name—manufactured by GC Dental Industries for 20 minutes. Others were all irradiated with GC Labolight LV-I for 5 minutes. After curing, five gaps A, B, C, D and E between parallel sections were determined under a projector or a reading microscope with an accuracy of 1 μm. Of the gaps A to E, a maximum gap is shown in the table.

TABLE

| | Photopolymerizable compound having therein at least one ethylenically unsaturated double bond being solid either crystalline or amorphous at 40° C. or lower | | | | Inorganic filler | |
|---|---|---|---|---|---|---|
| | Monofunctional | | | | | |
| | Methacrylate | | | | | |
| | Methoxypolyethylene glycol 1000 methacrylate (part by weight) | Acrylate Methoxypolyethylene glycol 1000 acrylate (Part by weight) | Polyfunctional | | Powdery glass (treated with silane coupling) (part by weight) | Colloidal silica (treated with silane coupling) (part by weight) |
| | | | Methacrylate <Note 3> (Part by weight) | Acrylate <Note 4> (part by weight) | | |
| Example 1 | | | 50 | 50 | 100 | |
| Example 2 | | | 50 | 50 | 50 | |
| Example 3 | | | 50 | 50 | 200 | |
| Example 4 | | | 80 | 20 | 100 | |
| Example 5 | | | 40 | 60 | 100 | |
| Example 6 | | | 50 | 50 | 100 | |
| Example 7 | | | 50 | 50 | 100 | |
| Example 8 | | | 50 | 50 | 100 | |
| Example 9 | | | 50 | 50 | 100 | |
| Example 10 | | | 50 | 50 | | 60 |
| Example 11 | | | 50 | 50 | 100 | |
| Example 12 | | | 50 | 50 | 100 | |
| Example 13 | | | 50 | 50 | 100 | |
| Example 14 | | | 50 | 50 | 100 | |
| Example 15 | | | 50 | 50 | 100 | |
| Example 16 | 100 | | | | 100 | |
| Example 17 | | 100 | | | 100 | |
| Example 18 | 50 | | 50 | | 100 | |
| Comparative Example 1 | | | 50 | 50 | 1 | |
| Comparative Example 2 | | | 50 | 50 | 550 | |
| Comparative Example 3 | | | 50 | 50 | 100 | |
| Comparative Example 4 | | | 50 | 50 | 100 | |
| Comparative Example 5 | | | 50 | 50 | 100 | |
| Comparative Example 6 | | | 50 | 50 | 100 | |
| Comparative Example 7 | Viscous liquid UDMA 100 part by weight at 40° C. or lower | | | | 150 | |
| Comparative Example 8 | Example wherein GC Surplate was used | | | | | |
| Comparative Example 9 | Example wherein GC Orthofast was used (powder to liquid ratio P/L = 100 g/50 ml) | | | | | |

| | Photopolymerization initiator | | | | |
|---|---|---|---|---|---|
| | α-diketone compound d,l camphorquinone (part by weight) | Ketal compound Benzil dimethyl ketal (part by weight) | Anthraquinone compound 1,2 benzanthraquinone (part by weight) | Thioxanthon compound Thioxanthon (part by weight) | Benzoin alkyl ether compound Benzoin isobutyl ether (part by weight) |
| Example 1 | 0.5 | | | | |
| Example 2 | 0.5 | | | | |
| Example 3 | 0.5 | | | | |
| Example 4 | 0.5 | | | | |
| Example 5 | 0.5 | | | | |
| Example 6 | 0.01 | | | | |
| Example 7 | 4.5 | | | | |

TABLE-continued

| | Dimethylaminoethyl methacrylate (part by weight) | 4-dimethylaminobenzoic acid methyl ester (part by weight) | Butyl hydroxy toluen (part by weight) | |
|---|---|---|---|---|
| Example 8 | 0.5 | | | |
| Example 9 | 0.5 | | | |
| Example 10 | 0.5 | | | |
| Example 11 | | 0.5 | | |
| Example 12 | | | 0.02 | |
| Example 13 | | | | 0.5 |
| Example 14 | | | | 0.5 |
| Example 15 | 0.5 | | | |
| Example 16 | 0.5 | | | |
| Example 17 | 0.5 | | | |
| Example 18 | 0.5 | | | |
| Comparative Example 1 | 0.5 | | | |
| Comparative Example 2 | 0.5 | | | |
| Comparative Example 3 | 0.0005 | | | |
| Comparative Example 4 | 6 | | | |
| Comparative Example 5 | 0.5 | | | |
| Comparative Example 6 | 0.5 | | | |
| Comparative Example 7 | 0.5 | | | |
| Comparative Example 8 | Example wherein GC Surplate was used | | | |
| Comparative Example 9 | Example wherein GC Orthofast was used (powder to liquid ratio P/L = 100 g/50 ml) | | | |

| | Reducing agent | | Polymerization inhibitor | |
|---|---|---|---|---|
| | Dimethylaminoethyl methacrylate (part by weight) | 4-dimethylaminobenzoic acid methyl ester (part by weight) | Butyl hydroxy toluen (part by weight) | Maneuverability before curing |
| Example 1 | 0.5 | | 0.03 | Good |
| Example 2 | 0.5 | | 0.03 | Good |
| Example 3 | 0.5 | | 0.03 | Good |
| Example 4 | 0.5 | | 0.03 | Good |
| Example 5 | 0.5 | | 0.03 | Good |
| Example 6 | 0.5 | | 0.03 | Good |
| Example 7 | 0.5 | | 0.03 | Good |
| Example 8 | 0.1 | | 0.03 | Good |
| Example 9 | 9 | | 0.03 | Good |
| Example 10 | 0.5 | | 0.03 | Good |
| Example 11 | 0.5 | | 0.03 | Good |
| Example 12 | 0.5 | | 0.03 | Good |
| Example 13 | 0.5 | | 0.03 | Good |
| Example 14 | 0.5 | | 0.03 | Good |
| Example 15 | | 0.5 | 0.03 | Good |
| Example 16 | 0.5 | | 0.03 | Good |
| Example 17 | 0.5 | | 0.03 | Good |
| Example 18 | 0.5 | | 0.03 | Good |
| Comparative Example 1 | 0.5 | | 0.03 | Viscous |
| Comparative Example 2 | 0.5 | | 0.03 | Too difficult to maneuver |
| Comparative Example 3 | 0.5 | | 0.03 | Good |
| Comparative Example 4 | 0.5 | | 0.03 | Good |
| Comparative Example 5 | 0.0005 | | 0.03 | Good |
| Comparative Example 6 | 12 | | 0.03 | Good |
| Comparative Example 7 | 0.5 | | 0.03 | Viscous |
| Comparative Example 8 | Example wherein GC Surplate was used | | | Good |
| Comparative Example 9 | Example wherein GC Orthofast was used (powder to liquid ratio P/L = 100 g/50 ml) | | | Different depending on viscosity |

| | Properties | | | | | |
|---|---|---|---|---|---|---|
| | \<Note 1\> Bending strength after curing ( ): Standard deviation (kg/cm$^2$) | \<Note 2\> Curing depth (mm) | \<Note 1\> Shrinkage upon polymerization (Linear shrinkage) (%) | Necessity of pressure pot | \<Note 1\> Maximum temperature of exothermic heat on curing (Sheet: 3 g; Powder: 2 g Liquid: 1 ml) (°C.) | \<Note 1\> Compatibility to master cast of gypsum (max. gap) (mm) |
| Example 1 | 718(21) | 6.21 | 0.13 | Not necessary | 26 | 0 |

| | | | | | | |
|---|---|---|---|---|---|---|
| Example 2 | 622(8) | 12.38 | 0.09 | Not necessary | 27 | 0 |
| Example 3 | 750(39) | 4.55 | 0.06 | Not necessary | 26 | 0 |
| Example 4 | 721(29) | 6.63 | 0.11 | Not necessary | 26 | 0 |
| Example 5 | 669(21) | 7.21 | 0.12 | Not necessary | 31 | 0 |
| Example 6 | 655(19) | 4.08 | 0.09 | Not necessary | 29 | 0 |
| Example 7 | 696(31) | 9.65 | 0.18 | Not necessary | 30 | 0 |
| Example 8 | 605(3) | 6.61 | 0.13 | Not necessary | 30 | 0 |
| Example 9 | 711(11) | 7.05 | 0.13 | Not necessary | 28 | 0 |
| Example 10 | 637(48) | 10.33 | 0.09 | Not necessary | 32 | 0 |
| Example 11 | 621(39) | 5.98 | 0.09 | Not necessary | 27 | 0 |
| Example 12 | 588(41) | 4.81 | 0.10 | Not necessary | 28 | 0 |
| Example 13 | 745(62) | 6.24 | 0.09 | Not necessary | 26 | 0 |
| Example 14 | 720(33) | 5.39 | 0.09 | Not necessary | 31 | 0 |
| Example 15 | 684(18) | 5.55 | 0.13 | Not necessary | 29 | 0 |
| Example 16 | 566(51) | 5.91 | 0.15 | Not necessary | 33 | 0 |
| Example 17 | 709(17) | 7.66 | 0.21 | Not necessary | 36 | 0 |
| Example 18 | 766(54) | 5.73 | 0.18 | Not necessary | 30 | 0 |
| Comparative Example 1 | 299(19) | 13.03 | 0.14 | Not necessary | 37 | 0.14 |
| Comparative Example 2 | 507(33) | 4.44 | 0.08 | Not necessary | 25 | 0 |
| Comparative Example 3 | 122(3) | 1.56 | 0.11 | Not necessary | 28 | 0 |
| Comparative Example 4 | Manupulation under ordinary indoor illumination being not possible | | | | | |
| Comparative Example 5 | 315(20) | 2.77 | 0.10 | Not necessary | 30 | 0 |
| Comparative Example 6 | Manupulation under ordinary indoor illumination being not possible | | | | | |
| Comparative Example 7 | 683(41) | 8.18 | 1.07 | Not necessary | 45 | 0.45 |
| Comparative Example 8 | 335(4) | — | 1.14 | Not necessary | — | 0 |
| Comparative Example 9 | 645(8) | — | 3.25 | Necessary | 69 | 0.89 |

Note 1

To prepare the sample containing photopolymerization initiators of a ketal and benzoin alkyl ether compound, the sample was irradiated with GC Permacure UC-I for 20 minutes. Other samples were made by irradiating GC Labolight LV-I for 5 minutes.

Note 2

The sample containing a ketal and benzoin alkyl ether compound was irradiated by GC Permacure UC-I for 20 minutes. Other samples were made by irradiating GC Labolight LV-I for 5 minutes.

Note 3

R: alkyl group

Note 4

$R_1$, $R_2$, $R_3$: alkyl group

In Examples 1 to 15, a mixture of the polyfunctional methacrylate with acrylate was used as the photopolymerizable compound that has therein at least one ethylenically unsaturated double bond and is a solid either crystalline or amorphous at 40° C. and lower. Used in Examples 16, 17 and 18 were the monofunctional methacrylate, the monofunctional acrylate and a mixture of the monofunctional methacrylate with the polyfunctional methacrylate, respectively.

In Examples 1 to 9 and 11 to 18, finely divided glass powders were used as the inorganic filler, and colloidal silica in Example 10. The inorganic fillers were all treated with the silane coupling agent so as to permit them to bond firmly to the photopolymerizable compound that has therein at least one ethylenically unsaturated double bond and is a solid either crystalline or amorphous at 40° C. and lower. In Example 1, the glass powders forming the inorganic filler were incorporated in a standard amount relative to the photopolymerizable compound that has therein at least one ethylenically unsaturated double bond and is a solid either crystalline or amorphous at 40° C. and lower. In Examples 2 and 3, however, the amount of the filler incorporated was decreased and increased, respectively. However, no problem arises whatsoever in connection with the obtained physical properties, since the amount of the finely divided glass powders incorporated falls in either case within the scope defined in the appended claims. This is also true of Examples 4 and 5 wherein the mixing ratio of the polyfunctional methacrylate with the polyfunctional acrylate varies.

In Examples 1 to 10 and 15 to 18, the photopolymerization initiators used were d,l-camphorquinone, and those in Examples 11, 12, 13 and 14 were benzyl dimethyl ketal, 1,2-benzanthraquinone, thioxanthon and benzoin isobutyl ether. Of these photopolymerization initiators, 1,2-benzanthraquinone is sufficiently effective in small amounts. The reducing agents used in Examples 1 to 14 and 16 to 18 were dimethylaminoethyl methacrylate, and 4-dimethylaminobenzoic acid methyl ester was used for that purpose in Example 15. The amount of d,l-camphorquinone added was reduced in Example 6 but it was increased in Example 7. The lesser the amount of d,l-camphorquinone added, the lesser the depth of curing, and vice versa. However, no actual problem arises at all, since the amount of d,l-camphorquinone comes in either case within the scope defined in the appended claims. The amount of the reducing agent dimethylaminoethyl methacrylate added was decreased in Example 8 but it was increased in Example 9. Since the depth of curing is largely dependent especially upon the amount of the photopolymerization initiators used, such decreases or increases in the amount of the reducing agent offer no problem in connection with the obtained physical properties. It is understood that the samples used in all the examples were previously molded into 2-mm thick sheets.

In Comparative Examples 1 to 6, use was made of the photopolymerizable compounds that have therein at least one ethylenically unsaturated double bond and are a solid either crystalline or amorphous at 40° C. and lower while, in Comparative Example 7, use was made of a photopolymerizable and polyfunctional methacrylate that has therein at least one ethylenically unsaturated double bond and is a liquid viscous at 40° C. and lower. In Comparative Example 8, use was made of GC Surplate composed mainly of shellac, while GC Orthofast of the powder/liquid type was employed in Comparative Example 9. The samples used in Comparative Examples 1 to 7 were all previously molded into 2-mm thick sheets, whereas the GC Surplate used in Comparative Example 8 was designed for the upper jaw and had a thickness of 1.5 mm. Referring here to GC Orthofast used in Comparative Example 9, it is general that the liquid is first applied onto a master cast of gypsum and the powder is then dusted thereover. In the present invention, however, the liquid and powder were previously weighed and then uniformly admixed together in a rubber cup so as to keep the powder to liquid ratio constant at 100 g to 50 ml. The obtained paste was then carefully fitted under pressure onto a master cast of gypsum of as uniform a thickess of 1.5 to 2 mm as possible. In Comparative Example 1, a mixture of the polyfunctional methacrylate with acrylate was used as the photopolymerizable compound that has therein at least one ethylenically unsaturated double bond and is a solid either crystalline or amorphous at 40° C. and lower, but the amount of the inorganic filler, i.e., finely divided glass powders, departed from the lower limit of the scope defined in the appended claims. In Comparative Example 2, on the contrary, the amount of finely divided glass powders serving as the inorganic filler departed from the upper limit of the scope defined in the appended claims. When the amount of the filler added departs from the lower limit, as is the case with Comparative Example 1, the sample tends to have an unsatisfactory property of becoming so sticky prior to curing that its bending strength after curing drops. Decreased amounts of the filler also result in slight increases in a maximum gap between the sample and a master cast of gypsum. If the quantity of the filler used departs from the upper limit defined, as is the case with Comparative Example 2, then the sample loses its flexibility and so breaks off or cracks during fitting. In Comparative Examples 3 and 5, the respective amounts of the photopolymerization initiator d,l-camphorquinone and the reducing agent dimethylaminoethyl methacrylate depart from the lower limits defined in the appended claims. The results are that insufficient polymerization takes place with drops in bending strength and curing depth. In Comparative Examples 4 and 6, the respective amounts of the photopolymerization initiator d,l-camphorquinone and the reducing agent dimethylaminoethyl methacrylate depart from the upper limits defined in the appended claims. The results are that too fast a curing reaction does not permit the compositions to have time to spare for dental manipulations under ordinary fluorescent illumination. Thus, it was impossible to prepare samples for the estimation of physical properties. In Comparative Example 7, use was made of a photopolymerizable compound based on urethane dimethacrylate that has therein at least one ethylenically unsaturated double bond and is a liquid viscous at 40° C. and lower. The resulting sample had a disadvantage of becoming extremely sticky in spite of the fact that as large as 150 parts by weight of finely divided glass powders were admixed. The sample shows so increased shrinkage upon polymerization (in terms of a linear shrinkage) that a maximum gap between the sample and a master cast of gypsum is increased with some drop in compatibility, since it transforms from a viscous liquid at normal temperature to a solid after polymerization. In Comparative Example 9 wherein methyl methacrylate is used as the main component, a maximum temperature of exothermic heat generated during curing becomes very much high and a polymerization shrinkage of as high as 3% is caused, so that a maximum gap between the sample and a master cast of gypsum is increased with a maximum drop in compatibility. In Comparative Example 9, the sample may also entail air bubbles by spatula handling or be foamed by the heat of polymerization during mixing. Thus, unless the sample is pressurized for polymerization in a pressure pot, it cannot be used for orthodontics.

EFFECT OF THE INVENTION

When full dentures or partial dentures for dentes defects are prepared with the dental photopolymerizable type resin compositions containing as the main component a photopolymerizable compound that has therein at least one ethylenically unsaturated double bond and is a solid either crystalline or amorphous at 40° C. and lower, such effects as mentioned below are obtained by making sheet-form base plates, sheet-form individual trays that are impresstion trays for individual patients for the purpose of taking the final impressions or sheet-form orthodontic resins to ameliorate malocclusion, restoring cleft palate and cheiloschisis and ameliorating bottle mouths.

1. The resin for photopolymerizable base plates, individual trays and orthodontics according to the present invention is previously molded into a sheet (having a thickness of 1.5 to 2.5 mm for base plates or orthodontic resins or 1.0 to 5.0 mm for individual trays). Because it contains as the main component a monomer which is a crystalline or amorphous solid at 40° C. and lower, it is unlikely to be softened and spread thin by touch of hands and fingers. Moreover, since the resin is previously kept constant in thickness, its thickness remains uniform, as compared with the powder/liquid type of resin being formed into a sheet. Thus, there is no possibility of breaking-off due to no stress concentrating on the thin portions.

2. The resin for base plates, individual trays and orthodontics according to the present invention generates less heat than does the powder/liquid type of cold-polymerizable resin composed mainly of polymethyl methacrylate and methyl methacrylate. Since little substantial thermal deformation occurs due to the generation of heat, the compatibility of a master cast of gypsum with respect to the base plates or orthodontic resins is greatly improved.

3. The resin for base plates, individual trays or orthodontics according to the present invention undergoes a phase transition from solid to solid. Thus, there is little substantial change in volume nor shrinkage upon polymerization. Thus, the compatibility of a master cast of gypsum with respect to the resin for base plates or orthodontics is greatly improved.

4. Since the resin for base plates, individual trays and orthodontics according to the present invention uses as its main component a photopolymerizable compound that is a crystalline or amorphous solid at 40° C. and lower, it shows no surface stickiness when comparing with a photopolymerizable sheet using a liquid viscous at 40° C. and lower and thus is greatly improved in terms of maneuverability when a sheet formed thereof is fitted under pressure onto a master cast of gypsum. Since that resin hardly adheres to the skin, neither eczema nor eruption is induced on the skin.

5. The photopolymerizable resin for orthodontics according to the present invention is of a paste type so previously defoamed that there is no need of any pressurization in a pressure pot for the purpose of the removal of air bubbles. Further, since no care is taken of the time when the resin is to be made pasty, it is possible to make an orthodontic resin of good compatibility within a short span of time but without recourse to any skilled hands. Still further, owing to no need of such repeated softening-by-heat as required for thermoplastic resins or waxes, it is easily achievable to prepare base plates or individual trays even for sophisticated cases such as the case of partial dentures.

6. The material for base plates and individual trays according to the present invention is incorporated therein with an inorganic filler treated on its surface, and is thus superior in its mechanical properties to thermoplastic resins or waxes. When used for base plates, therefore, it can thus sufficiently stand up to an occlusal pressure during bite taking on the one hand. When used for individual trays, on the other hand, it is possible to take precise impressions owing to no fear of breaking-off or deformation at all.

We claim:

1. A dental photopolymerizable resin composition consisting essentially of:

(a) at least one photopolymerizable compound that has therein at least one ethylenically unsaturated double bond present in a $CH_2=CHCOO-$ or $CH_2=C(CH_3)COO-$ group and is a solid either crystalline or amorphous at 40° C. and lower,
(b) an inorganic filler,
(c) a photopolymerization initiator, and
(d) a reducing agent.

2. A resin composition as defined in claim 1, wherein said photopolymerizable compound that has therein at least one ethylenically unsaturated double bond and is a solid either crystalline or amorphous at 40° C. and lower is a monofunctional methacrylate.

3. A resin composition as defined in claim 1, wherein said photopolymerizable compound that has therein at least one ethylenically unsaturated double bond and is a solid either crystalline or amorphous at 40° C. and lower is a polyfunctional methacrylate.

4. A resin composition as defined in claim 1, wherein said photopolymerizable compound that has therein at least one ethylenically unsaturated double bond and is a solid either crystalline or amorphous at 40° C. and lower is a monofunctional acrylate.

5. A resin composition as defined in claim 1, wherein said photopolymerizable compound that has therein at least one ethylenically unsaturated double bond and is a solid either crystalline or amorphous at 40° C. and lower is a polyfunctional acrylate.

6. A resin composition as defined in any one of claims 1 to 5, wherein the amount of said inorganic filler to be incorporated is 5 to 500 parts by weight per 100 parts by weight of said photopolymerizable compound that has therein at least one ethylenically unsaturated double bond and is a solid either crystalline or amorphous at 40° C. and lower.

7. A resin composition as defined in claim 1, wherein said photopolymerization initiator is at least one member selected from the group consisting of an α-diketone compound, a ketal compound, an anthraquinone compound, a thioxanthon compound, a benzoin alkyl ether compound and a derivative thereof.

8. A resin composition as defined in claim 1, wherein the amount of said photopolymerization initiator to be incorporated is 0.001 to 5 parts by weight per 100 parts by weight of said photopolymerizable compound that has therein at least one ethylenically unsaturated double bond and is a solid either crystalline or amorphous at 40° C. and lower.

9. A resin composition as defined in claim 1, wherein the amount of said reducing agent to be incorporated is 0.01 to 10 parts by weight per 100 parts by weight of said photopolymerizable compound that has therein at least one ethylenically unsaturated double bond and is a solid either crystalline or amorphous at 40° C. and lower.

* * * * *